US00PP34103P2

(12) United States Plant Patent
Ruigrok

(10) Patent No.: US PP34,103 P2
(45) Date of Patent: Apr. 5, 2022

(54) ***DAHLIA* PLANT NAMED 'BKDAMAGFCY'**

(50) Latin Name: *Dahlia hybrida*
Varietal Denomination: BKDAMAGFCY

(71) Applicant: BEEKENKAMP PLANTS B.V., Maasdijk (NL)

(72) Inventor: Sanne Helena Ruigrok, Hillegom (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/346,276

(22) Filed: Jun. 13, 2021

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC ... A01H 5/02; A01H 5/00; A01H 6/14; A01H 6/144
See application file for complete search history.

*Primary Examiner* — June Hwu
(74) *Attorney, Agent, or Firm* — C. Anne Whealy

(57) ABSTRACT

A new and distinct cultivar of *Dahlia* plant named 'BKDAMAGFCY', characterized by its upright to somewhat outwardly spreading and sturdy plant habit; vigorous growth habit; freely basal branching habit; dense and bushy growth habit; dark green-colored leaves; freely flowering habit; large decorative type inflorescences with bright yellow-colored ray florets; and good garden performance.

2 Drawing Sheets

Figure 1:
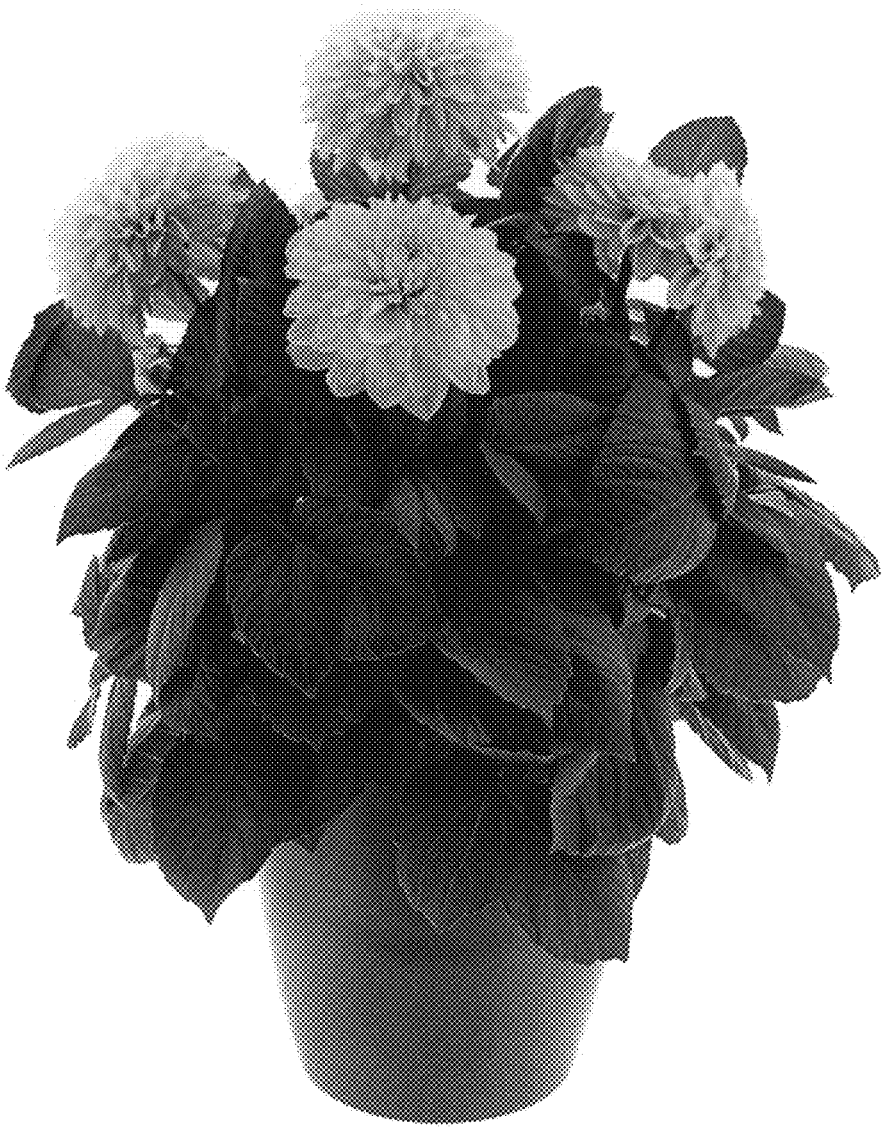

Botanical designation: *Dahlia hybrida.*
Cultivar denomination: 'BKDAMAGFCY'.

STATEMENT REGARDING PRIOR DISCLOSURES BY INVENTOR/APPLICANT AND ASSIGNEE

An European Community Plant Breeder's Rights application for the instant plant was filed by the Applicant/Assignee of the instant application, Beekenkamp Plants B.V. of Maasdijk, The Netherlands on Oct. 20, 2020, application number 2020/2575. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Dahlia* plant, botanically known as *Dahlia hybrida* and hereinafter referred to by the name 'BKDAMAGFCY'.

The new *Dahlia* plant is a product of a planned breeding program conducted by the Inventor in Hillegom, The Netherlands. The objective of the breeding program is to create new vigorous container *Dahlia* plants with large inflorescences with attractive ray floret coloration.

The new *Dahlia* plant originated from a cross-pollination in September, 2015 in Hillegom, The Netherlands of a proprietary selection of *Dahlia hybrida* identified as code number FET.S14.012.007, not patented, as the female, or seed, parent with a proprietary selection of *Dahlia hybrida* identified as code number FET.S13.024.013, not patented, as the male, or pollen, parent. The new *Dahlia* plant was discovered and selected by the Inventor as a single flowering plant from within the progeny of the stated cross-pollination in a controlled greenhouse environment in Hillegom, The Netherlands in September, 2016.

Asexual reproduction of the new *Dahlia* plant by terminal cuttings in a controlled greenhouse environment in Hillegom, The Netherlands since March, 2017 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMAGFCY'. These characteristics in combination distinguish 'BKDAMAGFCY' as a new and distinct *Dahlia* plant:

1. Upright to somewhat outwardly spreading and sturdy plant habit.
2. Vigorous growth habit.
3. Freely basal branching habit; dense and bushy growth habit.
4. Dark green-colored leaves.
5. Freely flowering habit.
6. Large, decorative type inflorescences with bright yellow-colored ray florets.
7. Good garden performance.

Plants of the new *Dahlia* differ primarily from plants of the female parent selection in inflorescence type as plants of the new *Dahlia* have decorative type inflorescences whereas plants of the female parent selection have single type inflorescences. In addition, leaves of plants of the new *Dahlia* are darker green in color than leaves of plants of the female parent selection.

Plants of the new *Dahlia* differ primarily from plants of the male parent selection in plant size as plants of the new *Dahlia* are larger than plants of the male parent selection. In addition, ray florets of plants of the new *Dahlia* are bright yellow in color whereas ray florets of plants of the male parent selection are pale yellow in color.

Plants of the new *Dahlia* can also be compared to plants of *Dahlia hybrida* 'BKDAMAGYL', disclosed in U.S. Plant Pat. No. 31,240. In side-by-side comparisons, plants of the new *Dahlia* differ from plants of 'BKDAMAGYL' in the following characteristics:

1. Plants of the new *Dahlia* have darker green-colored leaves than plants of 'BKDAMAGYL'.
2. Plants of the new *Dahlia* have smaller inflorescences than plants of 'BKDAMAGYL'.

Plants of the new *Dahlia* can also be compared to plants of *Dahlia hybrida* 'XXL Aztec Hidalgo', not patented. In side-by-side comparisons, plants of the new *Dahlia* differ from plants of 'XXL Aztec Hidalgo' in the following characteristics:

1. Plants of the new *Dahlia* have darker green-colored leaves than plants of 'XXL Aztec Hidalgo'.
2. Plants of the new *Dahlia* have slightly smaller inflorescences than plants of 'XXL Aztec Hildalgo'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1) is a side perspective view of a typical flowering plant of 'BKDAMAGFCY' grown in a container.

Figure 2:
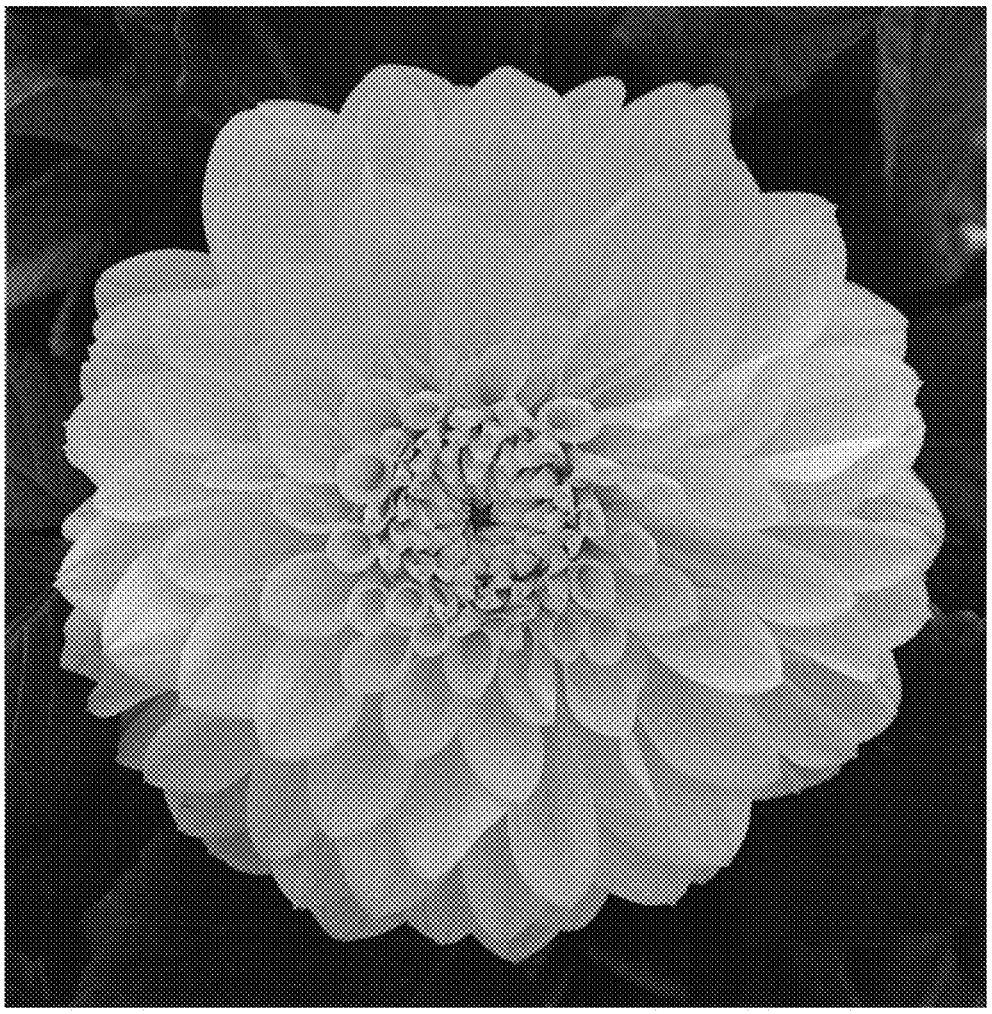

The photograph on the second sheet (FIG. 2) is a close-up view of a typical inflorescence of 'BKDAMAGFCY'.

DETAILED BOTANICAL DESCRIPTION

The aforementioned photographs and the following observations and measurements describe plants grown during the late winter and early spring in 20-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were eleven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAMAGFCY'.

Parentage:

*Female, or seed, parent*.—Proprietary selection of *Dahlia hybrida* identified as code number FET.S14.012.007, not patented.

*Male, or pollen, parent*.—Proprietary selection of *Dahlia hybrida* identified as code number FET.S13.024.013, not patented.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures about 21° C.

*Time to produce a rooted young plant, summer*.—About 21 days at temperatures ranging from 18° C. to 21° C.

*Time to produce a rooted young plant, winter*.—About 23 days at temperatures ranging from 19° C. to 21° C.

*Root description*.—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Upright to somewhat outwardly spreading and sturdy plant habit; overall plant shape, roughly globular; freely basal branching habit with about three primary branches each with about three secondary branches developing per plant; inflorescences held above the foliar plane on strong peduncles; bushy and dense growth habit; pinching is not required but will improve branching habit; vigorous growth habit and moderate growth rate.

*Plant height, soil level to top of foliar plane*.—About 33.3 cm.

*Plant height, soil level to top of floral plane*.—About 35.3 cm.

*Plant diameter or spread*.—About 44.4 cm.

*Lateral branches*.—Length: About 11.9 cm. Diameter: About 1.1 cm. Internode length: About 2.7 cm. Aspect: Primary branches are about 25° from vertical; secondary branches are about 30° from primary branch axis. Strength: Moderately strong to strong. Texture and luster: Smooth, glabrous; moderately glossy. Color, developing: Darker than 148B tinged with close to a blend of N186C, 200A and 200B. Color, developed: Close to 148A strongly tinged with close to N186C; at the internodes, close to 148A more strongly tinged with close to N186C.

Leaf & leaflet description:

*Arrangement*.—Leaves opposite and compound with typically three to five leaflets.

*Length, leaf*.—About 22.1 cm.

*Width, leaf*.—About 21.9 cm.

*Length, terminal leaflets*.—About 12.8 cm.

*Width, terminal leaflets*.—About 9.5 cm.

*Length, lateral leaflets*.—About 12.1 cm.

*Width, lateral leaflets*.—About 6.8 cm.

*Shape, leaves*.—Broadly ovate in outline.

*Shape, leaflets*.—Broadly ovate.

*Apex, leaflets*.—Apiculate.

*Base, leaflets*.—Short to long attenuate.

*Margin, leaflets*.—Coarsely serrate to dentate.

*Venation pattern, leaflets*.—Pinnate.

*Texture and luster, upper surface, leaflets*.—Mostly smooth, glabrous with venation, moderately pubescent; slightly rugose; slightly glossy.

*Texture and luster, lower surface, leaflets*.—Sparsely pubescent; slightly rugose; slightly glossy.

*Color*.—Developing leaflets, upper surface: Close to NN137A. Developing leaflets, lower surface: Close to between 147A and 147B. Fully expanded leaflets, upper surface: Darker than a blend of 147A and N189A; venation, close to a blend of N186C and 200A. Fully expanded leaflets, lower surface: Close to 191A; venation, close to N148A and 200C.

*Petioles*.—Length: About 4.2 cm. Diameter: About 7 mm by 10 mm. Strength: Moderately strong. Texture and luster, upper surface: Moderately pubescent; glossy. Texture and luster, lower surface: Smooth, glabrous; glossy. Color, upper surface: Close to N186C tinged with close to 200A. Color, lower surface: Close to 146C with axial stripes, close to 200B.

Inflorescence description:

*Appearance and arrangement*.—Decorative type inflorescences with ray florets forming acropetally on a receptacle; inflorescences positioned above and beyond the foliar plane on strong peduncles; inflorescences face mostly upright to slightly outwardly; freely flowering habit with about 27 developing and fully developed inflorescences per plant at one time; to date, disc floret development has not been observed.

*Fragrance*.—None detected.

*Flowering response and flowering period*.—Early flowering habit, plants begin flowering about 76 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 1.8 cm. Diameter: About 3.4 cm. Shape: Broadly ovate; involucral bracts reflexed. Texture and luster: Smooth, glabrous; glossy. Color: Close to 200C and 200D; proximally, close to 147A; distally, close to 4A; involucral bracts, close to NN137C.

*Inflorescence size*.—Diameter: Large, about 11.1 cm. Depth (height): About 6.5 cm.

*Receptacles*.—Height: About 5 mm. Diameter: About 1.3 cm. Shape: Lunate. Color: Close to 150D.

*Ray florets*.—Quantity per inflorescence and arrangement: About 260 arranged in about twelve whorls. Length: About 1.1 cm to 5.1 cm. Width: About 1.7 cm. Shape: Obovate to narrowly obovate; moderately carinate and moderately concave. Apex: Obtuse to broad and bluntly acute. Base: Cuneate. Margin: Entire. Aspect: About 40° from vertical. Texture and luster, upper surface: Smooth, glabrous; moderately velvety; matte. Texture and luster, lower surface: Smooth, glabrous; slightly velvety; mostly matte with venation, slightly glossy. Color: When opening, upper surface: More intense than 1A. When opening, lower surface: Close to 1A. Fully opened, upper surface: Close to 1A; venation, close to 161A; color becoming closer to 3A with subsequent development. Fully opened, lower surface: Close to 2B; venation, close to 161A to 161D; color becoming closer to 3B with subsequent development.

*Phyllaries*.—Quantity per inflorescence and arrangement: About 13 in an upper whorl and about nine in a lower whorl. Length, upper whorl phyllaries: About 2.2 cm. Width, upper whorl phyllaries: About 6 mm. Length, lower whorl phyllaries: About 1.6 cm. Width, lower whorl phyllaries: About 7 mm. Shape, upper whorl phyllaries: Narrowly oblong. Shape, lower whorl phyllaries: Oblanceolate; moderately carinate. Apex, upper whorl phyllaries: Obtuse. Apex, lower whorl phyllaries: Acute. Base, upper and lower whorl phyllaries: Cuneate. Margin, upper and lower whorl phyllaries: Entire. Texture and luster, upper and lower whorl phyllaries, upper and lower surfaces: Smooth, glabrous; glossy. Color, upper whorl phyllaries: Upper surface: Close to 174A; towards the base, close to 146A. Lower surface: Close to 177C to 177D; towards the base, close to 147A. Color, lower whorl phyllaries: Upper surface: Darker than 147A strongly tinged with close to 202A; towards the base, close to N186C. Lower surface: Close to NN137C; venation, close to a blend of 200A and 202A.

*Peduncles*.—Length, terminal peduncle: About 12.6 cm. Diameter, terminal peduncle: About 5 mm. Strength: Strong. Aspect: Mostly upright. Texture and luster: Smooth, glabrous; moderately glossy. Color: Close to 146B strongly tinged with close to 177A; proximally, close to N186C.

*Reproductive organs*.—Androecium: To date, none observed on plants of the new *Dahlia*. Gynoecium, present on ray florets: Quantity per floret: One. Pistil length: About 8 mm. Style length: About 6.5 mm. Style color: Close to 4A. Stigma diameter: About 2 mm. Stigma shape: Pointed. Stigma color: Close to 13A. Ovary color: Close to 150D. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Garden performance: Plants of the new *Dahlia* have been observed to have good garden performance, to tolerate high temperatures of about 35° C. and to be suitable for USDA Hardiness Zones 9 to 11.

It is claimed:

1. A new and distinct *Dahlia* plant named 'BKDAMAGFCY' as illustrated and described.

* * * * *